United States Patent [19]

Halsey

[11] 4,059,989
[45] Nov. 29, 1977

[54] NON-DESTRUCTIVE EXAMINATION OF AN ARTICLE PARTICULARLY A TIRE, WITH ULTRASONIC ENERGY

[75] Inventor: George H. Halsey, Indiana, Pa.

[73] Assignee: The Goodyear Tire & Rubber Company, Akron, Ohio

[21] Appl. No.: 749,545

[22] Filed: Dec. 10, 1976

[51] Int. Cl.$^2$ .................................. G01N 29/04
[52] U.S. Cl. ...................................... 73/598; 73/620; 73/629
[58] Field of Search ............... 73/67.5 R, 67.6, 67.7, 73/67.8 R, 67.8 S, 71.5 US

[56] References Cited

U.S. PATENT DOCUMENTS

| 2,378,237 | 6/1945 | Morris | 73/67.6 |
| 2,862,384 | 12/1958 | Renaut | 73/67.6 |
| 3,121,325 | 2/1964 | Rankin et al. | 73/67.8 S |
| 3,580,057 | 5/1971 | Seegmiller | 73/67.6 |
| 3,882,717 | 5/1975 | McCauley | 73/67.8 S |
| 3,910,104 | 10/1975 | Davies | 73/67.8 S |
| 3,910,124 | 10/1975 | Halsey | 73/67.6 |

FOREIGN PATENT DOCUMENTS

| 761,975 | 9/1953 | Germany | 73/67.6 |

Primary Examiner—Richard C. Queisser
Assistant Examiner—Stephen A. Kreitman
Attorney, Agent, or Firm—F. W. Brunner; R. S. Washburn

[57] ABSTRACT

Non-destructive examination of an article, particularly a tire for the presence, and particularly the depth below the surface, of an anomaly such as a discontinuity, void or foreign matter inclusion, employs ultrasonic energy. A transmitter of ultrasonic energy is disposed normal to the touching the surface of the article to be examined so as to feed ultrasonic energy thereinto. Ultrasonic energy receivers spaced apart from each other and from the trasmitter receive ultrasonic energy emergent or radiated from the surface of the article. With the tire, or other article, moving at a constant rate relative to the transmitter and receivers, a subsurface anomaly occludes or interrupts the energy beamed to the first receiver and then to the second. The time lapse and distance traveled between the two interruptions are proportional to the depth below the surface of the anomaly causing the interruptions. The energy received including the successive interruptions is displayed on an oscillograph. The foregoing abstract is not to be taken as limiting the invention of this application, and in order to understand the full nature and extent of the technical disclosure of this application, reference must be made to the accompanying drawing and the following detailed description.

8 Claims, 8 Drawing Figures

NON-DESTRUCTIVE EXAMINATION OF AN ARTICLE PARTICULARLY A TIRE, WITH ULTRASONIC ENERGY

This invention relates to the art of non-destructive testing using ultrasonic wave energy for locating sub-surface discontinuities in an article and, more particularly for determining the depth of such discontinuity below the surface of the article.

The present invention is particularly useful in testing of tires, particularly tires to be retreaded inasmuch as the invention provides a method and apparatus by which tires to be retreaded can be examined without exposure to water or other fluids. The location, particularly in depth below the surface, of a discontinuity is of particular interest in retreading tires to distinguish tires which can be successfully retreaded from those tires which cannot.

Broadly and briefly, the present invention provides a method of determining the location of an anomaly in an article and particularly in a vehicle tire without impairment of the integrity of the article which method comprises, moving the article at a constant rate in liquidfree space with respect to a reference line normal to a surface of the article, continuously impacting wave energy of 20 kilohertz to 100 kilohertz on said surface at the reference line, receiving wave energy emergent from the article at a plurality of locations spaced apart a predetermined distance in the direction of movement of the article, detecting a change in the emergent wave energy at each of said locations to provide a first signal at the first of said locations and a second signal at the second of said locations, measuring the time of travel by said article relative to the reference line between the first and second signal, and displaying or recording said time, said time being proportional to the depth of said anomaly below said surface.

Further, briefly and broadly, the invention provides an apparatus for carrying out the method comprising means for moving the article at a constant rate in a predetermined direction relative to said reference line while the article is supported in liquid-free space, a sonic energy transmitter disposed to impart sonic energy on said surface at said reference line, a pair of sonic energy receiver-transducer means spaced apart a predetermined distance along said direction with the reference line therebetween, detector means each having a window of predetermined shape for receiving a signal proportional to the sonic energy received respectively by each of said receiver-transducer means including changes in said signals effected by an internal anomaly in the article, means for measuring the time of travel by the article relative to said line between a change of signal in one of said receiver-transducer means and a corresponding change of signal in the other of the receiver-transducer means, and means for displaying or recording said time.

In order to acquaint persons skilled in the arts most closely related to the present invention, certain preferred embodiments thereof illustrating a best mode now contemplated for putting the invention into practice are described herein by and with reference to the annexed drawings forming a part of the specification. The embodiments shown and described herein are illustrative and as will become apparent to those skilled in these arts can be modified in numerous ways within the spirit and scope of the invention defined in the claims hereof.

Figure 1:
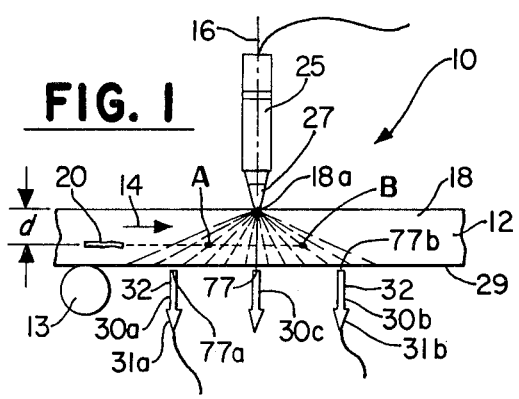
FIG. 1 is a schematic illustration of the method and apparatus in accordance with the invention.

Referring to FIG. 1; an article undergoing inspection for sub-surface anomalies is represented at 12. Means for supporting the article can be any convenient structure suited to the size and shape of the article and being readily available to persons skilled in the arts related hereto need not be illustrated. Likewise, means 13 for moving the article at a constant rate in the direction of the arrow 14 can be provided to suit the size and shape of the article.

For purposes of convenient description, a reference line 16 is shown perpendicular both to the direction of movement 14 and to the surface 18 below which the depth $d$ of an anomaly such as a discontinuity 20, if present, is desired to be measured.

The apparatus 10 comprises a transmitter 25 capable of producing wave energy in ultrasonic form having a range from about 20 kilohertz to as much as 100 kilohertz. The particular transmitter 25 in the apparatus 10 is a model 102 converter supplied by the Branson Sonic Power Company of Denver, Conn. and produces ultransonic wave energy of from 20 to 25 kilohertz along an oscillation or driving axis collinear with the reference line 16, i.e., perpendicular to the surface 18 of the article 12 and to the direction 14 of movement of he article.

Figure 7:
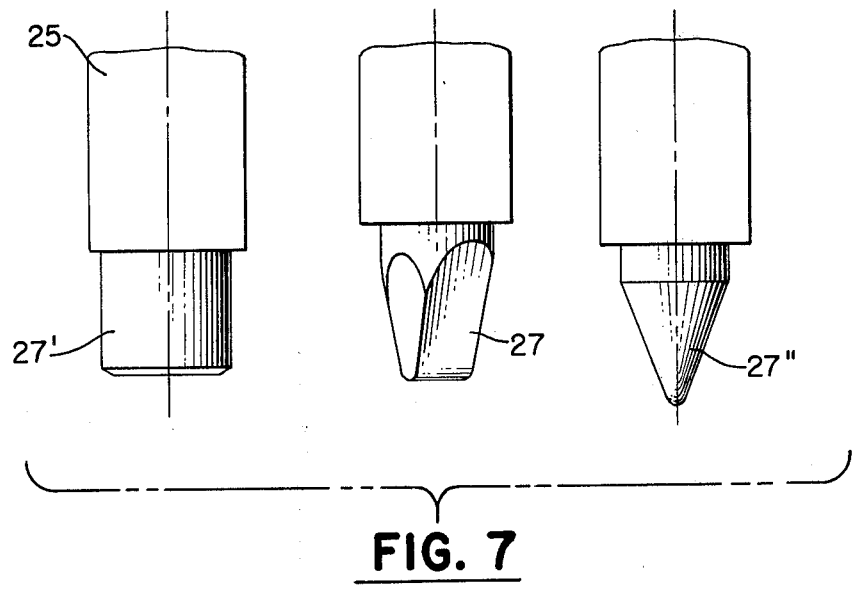
FIGS. 7 and 8 illustrate particular modifications of the apparatus of FIGS. 1 and 2.

The tip 27 of the transmitter 25 is modified in accordance with the invention to one of the forms illustrated in FIG. 7 and is brought into contact with the reference surface 18. The contact desired is a light touch or "kiss" contact sufficient to maintain contact during about one-half of the excursion of the oscillating tip 27. The power applied by the transmitter 25 is on the order of 35 watts and in any case is less than sufficient to overheat the material of the surface 18. The tip 27 in contact with the surface 18 defines a small contact area 18a from which sound wave energy is propagated into the article.

A portion of the wave energy originating at the contact area 18a and traveling through the article is radiated from the surface 29 of the article 12.

To receive the sound energy emanating from the surface 29, the apparatus includes two receivers 30a and 30b which are located close to the surface 29 and are spaced apart in the direction of movement 14 with the reference line 16 therebetween. The receivers 30a and 30b may be spaced symmetrically with respect to the line 16 but are not necessarily so spaced.

Each of the receivers includes a sonic energy transducer of the type commonly used in burglar alarms, provided in the apparatus 10 by Vernitron Corporation of Bedford, Ohio, as part No. 930015 and is capable of detecting sound wave radiations in the 20 to 25 kilohertz range. Each receiver, FIG. 8, also includes a horn 32 which is a hollow rectangular tube of about one-eighth inch by 1 inch (2.54 cm) inside and approximately 2 to 3 inches (5.08 to 7.62 cm) in length. The open end of the horn is disposed closely adjacent the surface 29 and provides a window 77 by which a selected portion of the energy radiating from the surface 29 is communicated by the tube to the transducer 31a or 31b.

It will be apparent from an inspection of FIG. 1 that as the article is moved in a direction 14, the leading edge of the discontinuity 20 will intercept at A the beam of ultrasonic energy between the area 18a and the window of the receiver 30a and thereby alter the continuous signal produced in the transducer 31a and that subsequently during the constant movement of the article the leading edge of the discontinuity will intercept at B the propagation of ultrasonic energy from the area 18a to the window of the receiver 30b, in turn causing a change in the continuous signal produced in the transducer 31b. It will also be apparent that the time $t$ of travel of the article over the distance between points A and B, at a constant rate of movement, is to the time of travel over the distance between the windows 77a and 77b as the depth $d$ from the surface 18 to the discontinuity 20 is to the line or plane defined by the windows 77a, 77b, which line or plane is close to or coincident with the surface 29. The depth $d$ is proportional to the time of travel from A to B.

Figure 2:
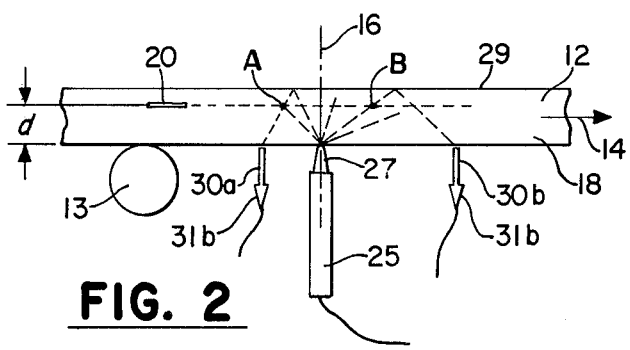
FIG. 2 is a schematic illustration of a modification of the method and apparatus of FIG. 1.

Referring to FIG. 2; the apparatus 35 is a modification of the apparatus 10 having the advantage with respect to the latter in that only one surface 18 of the article undergoing inspection need be accessible. Again, means for supporting the article 12 and means for providing a constant rate of movement in the direction 14 being entirely conventional have not been shown. The transmitter 25 is disposed with its oscillating axis collinear with the reference line 16 perpendicular to the surface 18 and to the direction of movement 14. Two receivers 30a, 30b identical to those described previously are spaced apart in the direction of movement 14 with their respective windows closely adjacent to the surface 18. In the apparatus 35 the receivers are required to be spaced non-symmetrically with respect to the reference line 16.

Ultrasonic energy propagated from the area of contact 18a of the tip 27 with the surface 18 is reflected at least in part from the opposing face 29 of the article. A portion of the reflected energy is radiated from the surface 18 and is admitted, in the area defined by the window 77 to each wave guide tube 32 and thus to the respective transducer 31a, 31b. The discontinuity 20, if present, will be seen from FIG. 2 to interrupt the path of energy reaching the receiver 30a at the point A thereby causing a change in the continuous signal emitted by the transducer 31a. As the leading edge of the discontinuity 20 reaches the point B, the ultrasonic energy reaching the receiver 30b is interrupted in the same manner causing a change in the continuous signal of the transducer 31b. As in the embodiment of FIG. 1, the time $t$ of travel of the article through the distance between points A and B, at a constant rate of movement, is directly proportional to the depth $d$ of the discontinuity 20 in the article from the surface 18.

Figure 3:
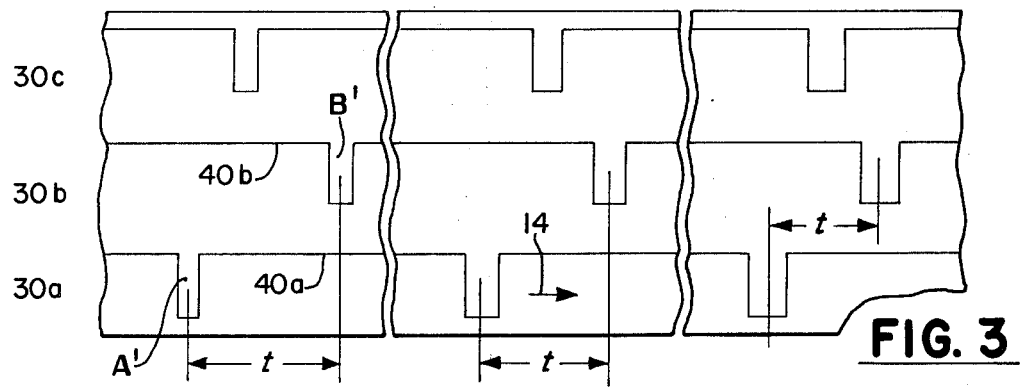
FIG. 3 is an idealized schematic view illustrating the measurement of the depth of a sub-surface discontinuity according to the invention.

In FIG. 3, there is shown an idealized line-recording of the signals received from the respective receivers representing conventional strip chart recordings of the signal output from 30a and from 30b. The third chart line, optionally provided for reference purposes, illustrates the signal from a third receiver 30c (see FIG. 4) disposed in close proximity to the surface 29 between the receivers 30a and 30b. The signal can be used to monitor the presence or absence of the energy emitted from the transmitter and for other purposes. The output from the respective transducers is amplified by generally conventional circuit means illustrated in FIG. 4 and fed to the conventional strip chart recorder wherein the charts of FIG. 3 are generated. The trace 40a represents the amplified signal produced by the receiver 30a and is seen to be constant in level in the absence of detectable discontinuities. The strip chart travels at a speed proportional to the constant rate of movement of the article. At the pip A' the trace 40a is displaced from its level, indicating a change in the signal produced by the interception of energy by the discontinuity 20 at the point A to the receiver 30a. Concurrently, the trace 40b of the signal produced from the receiver 30b continues at a constant level till it is displaced to form the pip B', which is indicative of the change in the signal received from the receiver 30b as a result of interception of the energy at the point B in the article under examination. The arrangement of the receivers 30a and 30b with respect to the propagating tip 27 of the transmitter define a triangle, the base of which is the spacing between the respective receivers 30a and 30b, the height of which is the distance between the tip 27 and the surface scanned by the windows of the respective receivers. Thus, by simple law of similar triangles, the depth $d$ below the surface 18 of the article to the leading edge of the anomaly is equal to the distance AB or to the measured time $t$ times the thickness or normal distance between the contact of point 27 and the surface scanned by the windows of the respective receivers, divided by the spacing in the direction of movement between the receiver 30a and the receiver 30b. Thus, in FIG. 3, it is seen to be a simple matter of measuring the distance in the direction of movement 14 between corresponding points of the pips A' and B' and adjusting for the preset ratio of article speed to chart speed. This distance is conveniently determined between the midpoints or centerlines of the respective pips. At the left portion of FIG. 3 the distance between the pips A' and B' represents a depth of a discontinuity below the surface 188 of 0.7 inch (17.8 mm). In the midportion of FIG. 3 the measured distance between the respective pips is found to indicate a depth below the surface 18 to a discontinuity 20 of 0.5 inch (12.7 mm). Similarly, in the righthand portion of FIG. 3, a distance measured between the respective pips in the direction of movement indicates a subsurface depth of 0.3 inch (7.6 mm) to the detected discontinuity.

It will be appreciated by persons skilled in the art that the actual trace of signals produced by the respective receivers will be irregular due to the presence of noise in such signal. Nevertheless, the apparatus can produce signals in the respective receivers with quantity and definition sufficient to determine the depth of a subsurface discontinuity with an accuracy of ±0.05 inch (1.27 mm), in an article, particularly a new or used tire.

Figure 4:
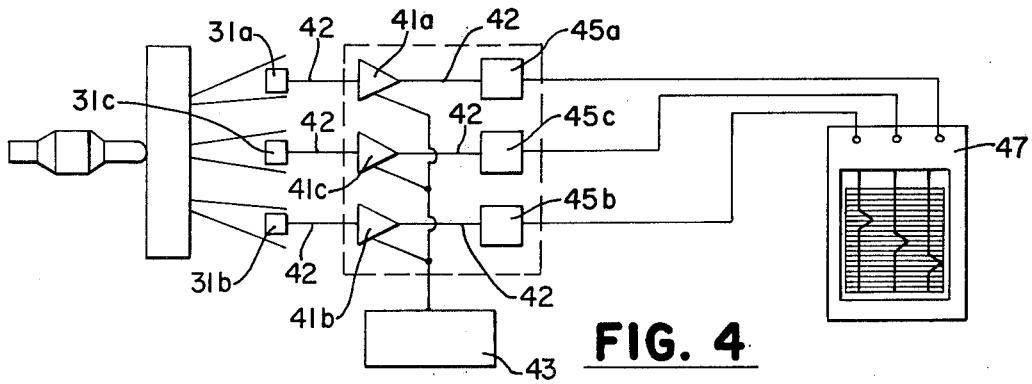
FIG. 4 is a schematic circuit diagram illustrating the essential elements of the apparatus.

In FIG. 4, the previously mentioned conventional circuit means includes the amplifiers 41a, 41b, 41c connected by the respective coaxial cables 42 to the receiver transducers 31a, 31b, 31c. A suitable power supply 43 feeds the amplifiers. The amplified signal from each of the amplifiers is processed respectively by the DC-AC converters 45a, 45b, 45c and fed to the appropriate terminal of a multiple row strip chart recorder 47 or oscillograph. The dashed outline of FIG. 1 indicates a unitized assembly of the three amplifiers and converters. The circuit means is selected for compatability with the selected sonic energy transmitter 25, particularly its frequency, which in the present embodiment is 20 kilocycles.

It will be observed that the time of the travel of the article can equally well be converted by means known to technicians to actuate a galvanometer to display the depth $d$ so measured, or to actuate an audible or visible device to indicate the acceptability or non-acceptability of the article in regard to the depth of depths of one or more anomalies therein. The means for and the step of displaying or recording will be understood to include such equivalents.

It is important to note that the article undergoing examination is not submerged in a liquid couplant but is instead in free air space. The use of liquids, and particularly water, in contact with a tire to be retreaded is believed to be undesirable, especially so when reinforcing cord elements thereof may be exposed. The arrangement of the ultrasonic transmitter 25 with respect to the surface 18 of the article is sometimes referred to as "air coupling" because of the absence of customary liquid coupling, usually water, by which coupling fluid the ultrasonic energy is communicated to the article undergoing examination. In the present apparatus and method, however, the coupling between the transmitter and the article to be examined may better be described as direct coupling because in the preferred arrangement the ultrasonic transmitter tip 27 is in direct contact, lightly touching the surface 18 of the article. It is also to be noted particularly that ultrasonic energy is propagated in the article continuously and that ultrasonic energy radiated from the surface of the article is sampled by the receivers which, in the absence of an anomaly, a discontinuity, produce a continuous signal. The present method and apparatus are distinguished completely from ultrasonic testing devices commonly referred to as "pulse echo" arrangements wherein the ultrasonic energy is propagated, by liquid coupling, into the article in bursts and by receivers which necessarily receive ultrasonic energy radiated from the article intermittently.

Figure 5:
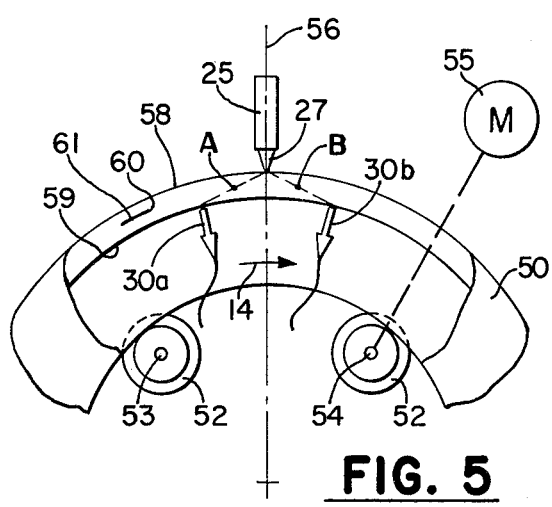
FIG. 5 is a schematic elevation view in partial cross-section illustrating the application of the invention in apparatus for inspecting a tire.

In FIG. 5 the article undergoing examination is a tire 50. Means for supporting the tire are provided by pairs of flanged wheels 52 each pair being mounted on one of a pair of parallel shafts 53, 54 rotatably supported on a structure (not shown). Each of the flanged wheels engages a bead portion of a tire to support the tire for rotation about its own central axis. Means for rotating the tire are provided by a constant speed motor drive 55 connected to rotate the flanged wheels at a constant rate so that the surface 58 of the tire undergoing examination is moved at a constant speed relative to the reference line 56. Like the apparatus 10 of FIG. 1, the present apparatus includes a transmitter 25 having a tip 27 disposed collinearly with the reference line in contact with the surface of the tire being examined. The receivers 30a and 30b are disposed removably within the tire cavity with the respective wave guide windows in close proximity to the inner surface 59 of the tire. As in the apparatus 10 the receivers are spaced oppositely of the reference line in the direction of movement rotation. The leading edge 60 of the discontinuity 61 first interrupts at the point A the energy beam extending from the tip 27 to the window of the receiver 30a. As movement continues in the direction 14, the leading edge of discontinuity then interrupts at the point B the beam of energy from the tip 27 to the window of 30b. The respective continuous signals as displayed on the strip chart, FIG. 3, are successively interrupted forming the pips A' in the first channel and B' in the second channel. The displacement and/or time in the direction of movement is proportional to the depth of the sub-surface discontinuity with respect to the surface 58 of the tire.

Figure 6:
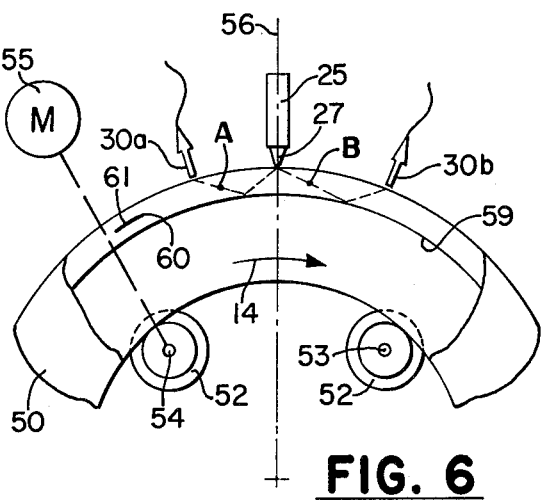
FIG. 6 is a schematic elevation view partially in section illustrating the application of the modification of FIG. 2 in inspection of a tire.

In the apparatus illustrated in FIG. 6, means for supporting the tire 50 and means for effecting rotation of the tire about its own axis in the direction are identical to that as described as to FIG. 5. The arrangement of the transmitter 25 and the respective receivers 30a and 30b corresponds to that described in connection with FIG. 2, in the apparatus 35. It will be apparent that this arrangement has advantages with respect to examination of tires in that it becomes unnecessary to locate either the transmitter or the receivers within the cavity of the tire. As the tire is rotated in the indicated direction, the leading edge 60 of a discontinuity 61 arriving at the point A intercepts a beam of the energy propagated by the transmitter tip 27 and reflected from the inner surface 59 of the tire thus effecting a change in the signal output from the receiver 30a. As the rotation at the constant rate continues, the leading edge of the discontinuity then interrupts the beam of energy at B extending from the propagation surface at the tip 27 and thence to the inner surface 59 of the tire being reflected then to the outer surface 18 where it effects a change in the signal output of the receiver 30b. The respective signals are amplified and displayed by the respective traces 40a and 40b having the pips A' and B'. The time and/or the distance between the pips A' and B' are proportional to the depth of the sub-surface discontinuity 61 below the surface engaged by the tip 27.

It will be apparent that receivers 30a, 30b can be disposed in a similar manner to that described in connection with either FIG. 5 or FIG. 6 thereby to determine the respective depths of a discontinuity which may be found, for example, along the circumferential centerline of the tire, as well as along the respective shoulder portions of the tire displaced with respect to the plane of FIGS. 5 and 6.

With reference to FIG. 7; a transmitter 25 is conventionally furnished with a cylindrical tip 27' terminating in a plane circular face perpendicular to the oscillation axis. In the present apparatus it is believed advantageous to replace the conventional tip 27' with a tip 27 having a predetermined small area of engagement with the surface 18 of the article. This small surface area is provided by forming the tip 27 as a cone, as at 27", having a small spherical radius at its apex. Alternatively, the tip 27 can be formed as a wedge or chisel having a short cylindrical surface of small radius at its apex. It has been determined experimentally that the smaller the area of contact between the tip and the surface of the article, the more sharply defined can be the change in signal received by the respective receivers.

Figure 8:
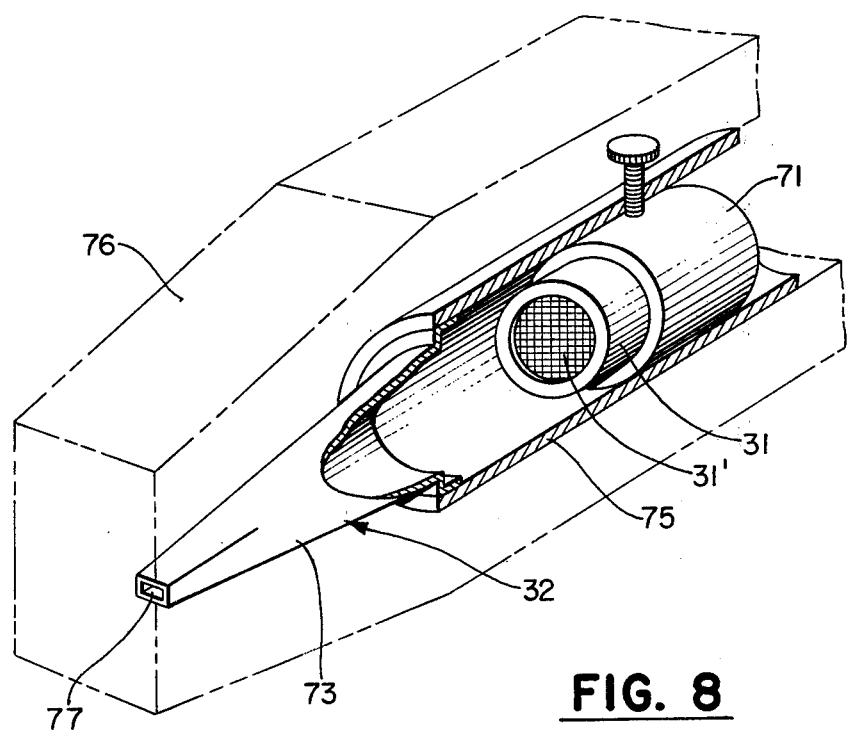

In FIG. 8, the ultrasonic energy receiver 30 is illustrated in longitudinal cross-section, the transducer 31 being conventionally mounted in a ferrule 71. The wave guide tube 32 of the receiver is formed of four plane walls affixed to a sleeve 75 and telescopically adjustable with respect to the ferrule. The wave guide extends approximately 3 (7.62 cm) inches between the face 31' of the transducer 31 and the window 77.

Surprisingly, the sonic energy radiating from the surface can be conducted without appreciable loss by a wave guide tube, such as the tube 32, to the receive-transducer with the advantage that the sonic energy wave front can be "sampled" in a well-defined area. The path of the energy wave between transmitter and receiver is as a result capable of determining the location of an anomaly with respect to the surface of an article such as an uninflated tire within satisfactorily narrow limits.

Advantageously, in certain applications, the wave guide tube of the receiver 30 may be surrounded by an envelope of energy insulation, such as a semi-rigid foam of a polyurethane extending to contact with the surface of the article adjacent to the window and along the length of the receiver so that the transducer 31 is not subjected to ultrasonic energy other than that radiated into the window of the wave guide.

While certain representative embodiments and details have been shown for the purpose of illustrating the invention, it will be apparent to those skilled in the art that various changes and modifications may be made therein without departing from the spirit or scope of the invention.

What is claimed is:

1. Method of determining the location of an anomaly in an article and particularly in a vehicle tire without impairment of the integrity of the article which method comprises, moving the article at a constant rate in liquidfree space with respect to a reference line normal to a surface of the article, continuously impacting wave energy of 20 kilohertz to 100 kilohertz on said surface at the reference line, receiving wave energy emergent from the article at a plurality of locations each spaced in the direction of movement of the article, detecting a change in the emergent wave energy at each of said locations to provide a first signal at the first of said locations and a second signal at the second of said locations, measuring the time of travel by said article relative to the reference line between the first and the second said signal, and displaying or recording said time, said time being indicative of the depth of said anomaly below said surface.

2. Apparatus for determining the location of an anomaly in an article comprising means for moving the article at a constant rate in a predetermined direction relative to a reference line while the article is supported in liquid-free space, an energy transmitter disposed to touch the surface of said article during a portion only of the vibratory excursion of said transmitter to impart ultrasonic energy on said surface at said reference line for passing energy through the article, a pair of energy receiver-transducer means spaced apart a predetermined distance along said direction including detector means each having a window of predetermined shape for receiving a signal proportional to the energy received respectively by each of said receiver-transducer means including changes in said signals effected by a subsurface anomaly in the article, means for measuring the time of travel by the article relative to said line between a change of signal in one of said receiver-transducer means and a corresponding change of signal in the other of the receiver-transducer means, and means for displaying or recording said time as indication of said location.

3. Apparatus as claimed in claim 2, said detector means being disposed closely adjacent a surface of the article opposite to the first-mentioned surface.

4. Apparatus as claimed in claim 2, said detector means being disposed closely adjacent the first-mentioned surface such that energy input by the transmitter to the article traverses the article twice between the transducer and the respective receiver-transducer.

5. Apparatus as claimed in claim 2, including an energy absorber disposed adjacent said surface between the transmitter and each of said receivers to minimize reception of energy from the transmitter by the receivers other than through the article.

6. Apparatus as claimed in claim 2, each said receiver transducer including a horn having a predetermined area window disposed adjacent said article to receive selectively a defined portion of the energy emergent from the article at a predetermined distance from the reference line.

7. Apparatus as claimed in claim 6, said horn comprising a wave guide tube having said receiver transducer telescopically accommodated therein for adjustment longitudinally in said tube.

8. The apparatus as claimed in claim 2, said article being an uninflated tire.

* * * * *